United States Patent [19]

Matschiner et al.

[11] Patent Number: 5,401,662
[45] Date of Patent: Mar. 28, 1995

[54] METHOD AND REAGENT FOR THE DETERMINATION OF WATER

[75] Inventors: Hermann Matschiner; Claus-Peter Maschmeier, both of Halle, Germany

[73] Assignee: Riedel-de Haen Aktiengesellschaft, Seelze, Germany

[21] Appl. No.: 121,176

[22] Filed: Sep. 13, 1993

[30] Foreign Application Priority Data

Sep. 14, 1992 [DE] Germany ............... 42 30 717.1

[51] Int. Cl.$^6$ ............................... G01N 33/18
[52] U.S. Cl. .................... 436/42; 436/106; 436/111; 436/112; 436/122; 436/163
[58] Field of Search ............ 436/39, 40, 42, 111, 436/122, 163, 180, 112, 106

[56] References Cited

U.S. PATENT DOCUMENTS

| 3,682,783 | 8/1972 | Dahms | 204/1 T |
|---|---|---|---|
| 3,749,659 | 7/1973 | Dahms | 204/195 T |
| 4,355,998 | 10/1982 | Verbeek et al. | 436/39 |
| 4,378,972 | 4/1983 | Scholz | 436/42 |
| 4,385,124 | 5/1983 | Verbeek et al. | 436/42 |
| 4,416,997 | 11/1983 | Fischer et al. | 436/42 |
| 4,429,048 | 1/1984 | Scholz | 436/42 |
| 4,619,900 | 10/1986 | Scholz | 436/42 |
| 4,720,464 | 1/1988 | Kuwata et al. | 436/42 |
| 4,740,471 | 4/1988 | Scholz | 436/42 |

FOREIGN PATENT DOCUMENTS 1068810  1/1984  U.S.S.R. .

Primary Examiner—N. Bhat
Attorney, Agent, or Firm—Connolly & Hutz

[57] ABSTRACT

In the method for the determination of water, the sample is admixed with a molar 1:1 adduct of sulphur dioxide with an amine having a $pK_A$ of more than 6, dissolved in an aprotic solvent, and is oxidized with iodine.

15 Claims, No Drawings

METHOD AND REAGENT FOR THE DETERMINATION OF WATER

The invention relates to a method and a reagent for the determination of water.

The determination of water according to Karl Fischer has developed into the preferred method. This determination is based on the Karl Fischer reaction:

$$SO_2 + ROH + B \rightarrow BHSO_3R \quad (1)$$

$$BHSO_3R + I_2 + H_2O + 2\,B \rightarrow BHSO_4R + 2BHI \quad (2)$$

B=base, ROH=alcohol

In this determination, the reagent comprises an alkyl sulphite, which is oxidised to alkyl sulphate in the presence of water (G. Wünsch and A. Seubert, Fresenius Z. Anal. Chem. 334 (1989) 16–21). The Karl Fischer titrations are therefore carried out in alcoholic solution or, if other solutions are used, for example propylene carbonate, in the presence of the stoichiometric or a minimum amount of alcohol.

The alcohol limits the applicability of the Karl Fischer titration, as it can interfere or cause side reactions. Thus it is possible for acids, together with the alcohol contained in the reagents, to take part in an esterification which results in the formation of water (E. Scholz, Fresenius Z. Anal. Chem. 303 (1980) 203–207). Fats and long-chained hydrocarbons are only sparingly soluble in alcohols, which had led to the use of halogenated hydrocarbons as a solvent component, a questionable practice, however, because of their toxicity.

When water is determined in ketones, ketal formation may occur, which similarly proceeds with the elimination of water, but which can be repressed if the chloroethanol, which is toxic, is used as a solvent (E. Scholz, Karl Fischer titration, Springer Verlag 1984, Heidelberg, New York, Tokyo).

The use of reagents which contain $SO_2$ and pyridine has also been described, even by Karl Fischer, for example (Angew. Chemie 48 (1935), 394–396). Pyridine is then used in excess. It was found, however, that the determinable water equivalent is heavily dependent on the experimental conditions. One of the reasons is the pyridine-$SO_3$ adduct formed, which takes part in a water-simulating side reaction and falsifies the result of the analysis. While it is possible to obtain better values by adding alcohol (D. M. Smith, W. M. D. Bryant, J. M. Mitchel, J. Am. Chem. Soc. 61 (1939), 2407), the drawbacks of the alcohol are then observed once more. Moreover, working with pyridine in routine analyses is problematic on account of its toxicity and unpleasant smell.

The object of the invention stated in the claims is to find a novel method and a novel reagent for the determination of water which do not have the drawbacks of the reagents containing alcohol and/or pyridine.

In the method according to the invention for the quantitative determination of water in a water-containing sample, the sample is mixed with a molar 1:1 adduct of sulphur dioxide to an amine having a $pK_A$ of more than 6, dissolved in an aprotic solvent, and is oxidised with iodine. Based on the iodine consumption, the water content of the sample can then be calculated.

In applying the method, the sample is mixed, in particular, with a molar 1:1 adduct of sulphur dioxide to trimethylamine, dissolved in an aprotic solvent.

For the volumetric determination of water, the water-containing sample a) is mixed with the molar 1:1 adduct of sulphur dioxide to an amine, dissolved in the aprotic solvent, and is then titrated with an iodine solution, or b) is dissolved in an aprotic solvent and is titrated with a solution which, in an aprotic solvent, contains a molar 1:1 adduct of sulphur dioxide to an amine having a $pK_A$ of more than 6 and iodine.

For the coulometric determination of water, the water-containing sample is mixed with a solution which, in an aprotic solvent, contains a soluble iodide in addition to the molar 1:1 adduct of sulphur dioxide to an amine, and iodine is generated therefrom by anodic oxidation.

The reagent according to the invention can be a two-component or a single-component reagent for the volumetric determination of water or a reagent for the coulometric determination of water. A two-component reagent according to the invention for the volumetric determination of water comprises a solvent component and an iodine solution as a titrant component, and is characterised in that the solvent component contains a molar 1:1 adduct of sulphur dioxide to an amine having a $pK_A$ of more than 6 in an aprotic solvent.

A single-component reagent according to the invention for the volumetric determination of water contains, in an aprotic solvent, a molar 1:1 adduct of sulphur dioxide to an amine having a $pK_A$ of more than 6 and iodine.

A reagent according to the invention for the coulometric determination of water contains, in an aprotic solvent, a molar 1:1 adduct of sulphur dioxide to an amine having a $pK_A$ of more than 6 and an iodide.

The amine having a $pK_A$ of more than 6 may be, for example, an optionally substituted aliphatic, cyclic, heterocyclic or aromatic amine. Suitable amines of this type include: trialkylamines, such as trimethylamine, triethylamine, tri-n-propylamine, tri-n-butylamine, N,N-dimethylethylamine, N,N-diethylmethylamine, N,N-dimethyl-n-butylamine, also N,N,N',N'-tetramethylethylenediamine, imidazole, 1-ethylimidazole, 1-methylpiperidine, 1-ethylpiperidine, 1,2-dimethylpyrrolidine, 1-methylpyrrolidine, N-ethylmorpholine, N-methylmorpholine. It is also possible to use mixtures of different amines in preparing the molar 1:1 adducts. The amines trimethylamine, imidazole, N,N,N',N'-tetramethylethylenediamine or mixtures thereof are preferably used in preparing the molar 1:1 adducts with sulphur dioxide. The use of the molar 1:1 adduct of sulphur dioxide to trimethylamine is especially preferred.

The molar 1:1 adducts of sulphur dioxide and the amine having a $pK_A$ of more than 6 are easily prepared by combining the components amine and $SO_2$, in an inert solvent or diluent if required.

Suitable aprotic solvents for carrying out the method according to the invention and for preparing the reagents according to the invention include: ethers, such as diisopropyl ether, dibutyl ether, dioxane, tetrahydrofuran, nitriles, such as acetonitrile, esters, such as ethyl acetate, ethyl propionate, isobutyl acetate, n-butyl acetate, ethylene carbonate, propylene carbonate, butyrolactone, halogenated hydrocarbons, such as chloroform, carbon tetrachloride, 1,2-dichloropropane, methylene chloride, acid amides, such as dimethylformamide, dimethylacetamide, N-methylpyrrolidone, ketones, such as acetone, methyl ethyl ketone, diethyl ketone, cyclohexanone, methylcyclohexanone, acetylacetone and other aprotic solvents, such as, for example, dimethylacetal. Instead of an aprotic solvent it is also possible to use a mixture of a plurality of aprotic solvents.

Preferred aprotic solvents are acetonitrile, propylene carbonate, ethyl acetate, tetrahydrofuran, dioxane, dimethylformamide or methylene chloride or mixtures thereof.

To prepare the reagent according to the invention, one or more of the molar 1:1 adducts of sulphur dioxide to an amine having a $pK_A$ of more than 6 are dissolved in the aprotic solvent or solvent mixture and/or are generated by combining the components amine and sulphur dioxide in a molar ratio of 1:1. The concentration generated in the aprotic solvent or solvent mixture of the active component of the molar 1:1 adduct by dissolving or by combining the components is preferably from 0.01 to 5 mol/l, particularly preferably from 0.25 to 1.5 mol/l. The solution thus prepared represents the solvent component of a two-component reagent according to the invention. The associated titrant component used is a solution of iodine in a preferably aprotic solvent or solvent mixture. In doing so, the same solvent or solvent mixture is used for the titrant component as for the solvent component.

It is possible to prepare a single-component reagent according to the invention from the solvent component by dissolving additional iodine. Iodine may be added, for example, in an amount of ⅓ of the amine-$SO_2$ adduct concentration. If the reagent is to be used for the coulometric determination of water, the addition of iodine is replaced by an addition of iodide or a mixture of iodides. In doing so, iodides are used which are soluble in the aprotic solvent or solvent mixture.

The determination of water according to the invention proceeds, in contrast to the Karl Fischer reaction (1) and (2), according to the following overall equation (3):

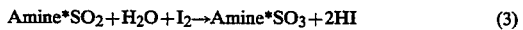

$$\text{Amine}^*SO_2 + H_2O + I_2 \rightarrow \text{Amine}^*SO_3 + 2HI \quad (3)$$

Based on the iodine consumption, the water content is calculated. In contrast to the pyridine-$SO_3$ adduct, the amine-sulfphur dioxide adduct in the molar ratio 1:1 used according to the invention does not show any water-simulating side reaction.

The necessary iodine can be added or can be generated by anodic oxidation from added iodide. During the determination of water, the added or anodically generated iodine is reduced to iodide by the reaction with sulphur dioxide and water. When there is no more water, free iodine is left over. The iodine excess can be used for indicating the end-point, for example for visual or for photometric indication. It is also possible to indicate it electrochemically, for example bipotentiometrically or biamperometrically.

One way of carrying out the determination of water is to combine or mix the water-containing sample with the solvent component of a two-component reagent according to the invention, for example to add the sample to the solvent component, and then to carry out a titration using a solvent of iodine or of the titrant component of the two-component reagent.

Another way of carrying out the determination of water is to dissolve the water-containing sample by combining it with an aprotic solvent or solvent mixture and then to titrate it with a single-component reagent according to the invention.

The coulometric determination of water can be carried out, for example, by introducing an iodide-containing coulometric reagent according to the invention into a coulometric cell, preferably into a divided cell and then, according to the cell construction, adding the sample and electrolysing, by switching on the electrolysis current, until the water present has been converted.

Prior to the determination of water proper, any water contained in the solvent must be removed in a blank titration (by pre-electrolysis in the case of a coulometric determination).

The reagent according to the invention and the method according to the invention can easily be adapted to the various requirements of the titration appliances used in practice and/or to the methods of determination used and/or to the particular properties of the sample.

Thus the reagent according to the invention, when used for the coulometric determination, is admixed with one or more soluble iodides, for example inorganic iodides, such as sodium iodide, or iodides of organic cations, such as tetrabutylammonium iodide, imidazole hydrogen iodide or trimethylamine hydrogen iodide. As coulometric appliances require a reagent having a conductivity of between 1 and 10 mS/cm, it may be necessary to add additional supporting electrolytes. These may be soluble inorganic salts. Preferably, dissociating organic salts such as, for example, tetrabutylammonium chloride, diethanolamine hydrogen bromide, or alternatively soluble iodides are used.

To indicate the end-point, both in volumetric analysis and in coulometric titration, frequent use is made of bipotentiometric or biamperometric indication. In order to obtain which stabilise the end-point. Appropriate substances include reproducible end-points it may be expedient to add substances supporting electrolytes, such as are used in coulometric analysis. The addition of iodides is also possible, preferably in concentrations of from 0.01 to 0.1 mol/l. Substances having a buffering action, such as, for example, carboxylic acids such as, for example, acetic acid, or their salts, such as, for example, sodium acetate, or weak nitrogen bases having $pK_A$ values, for example, between 4 and 9, or their salts, may likewise have a stabilising effect.

As the samples to be analysed are not always soluble in the reagent used, the reagent has to be admixed, in cases like these, with solubilisers for non-polar samples, formamide for salts and protein-containing samples or halogenated hydrocarbons for fats and fat-like substances.

To neutralize acidic samples, suitable bases can be added to the reagent, for example nitrogen bases such as imidazole, or salts or carboxylic acids, such as tetramethylammonium acetate, trimethylammonium acetate, tetrabutylammonium benzoate or lithium propionate. Alkaline samples are neutralised with an acid, the reagent is admixed, for example, with a weak acid, such as acetic acid, propionic acid, butyric acid or alternatively benzoic acid. A buffering action against acids and bases is achieved by adding buffer substances, for example diethanolammonium benzoate or imidazolium acetate.

WORKING EXAMPLES

EXAMPLE 1

3 g of the molar 1:1 trimethylamine-sulphur dioxide addition compound is dissolved in 45 ml of acetonitrile. By metering in a 0.05 molar iodine solution (solvent acetonitrile), a pretitration is carried out in a commercial Karl Fischer automatic titrator. The sample containing between 2 and 5 mg of water (for example water-containing acetonitrile) is dosed and titrated to completion with the iodine solution.

EXAMPLE 2

In a titration vessel sealed against the ingress of moisture, 3 g of trimethylamine-sulphur dioxide addition compound are dissolved in 45 ml of acetonitrile. By metering in a 0.125 molar iodine solution (solvent acetonitrile), a defined excess of approximately 0.5 ml of iodine solution is generated. The sample containing between 4 and 15 mg of water is then dosed (for example a mixture of water and acetonitrile) and is then titrated further with the iodine solution until the equivalence-point is exceeded. The volume difference of the iodine solution between the equivalence-points is used to calculate the amount of water contained in the sample. The determination of the equivalent-point is carried out photometrically with the aid of an immersion photometer using the green light of a light-emitting diode.

EXAMPLE 3

According to Example 2, in samples 100 µl of acetone with a water content of 4.02 mg in each case, the following amounts of water were found:

4.06 mg, 4.06 mg, 4.08 mg, 4.13 mg, mean value: 4.08 mg.

In 50 µl of acetone with a water content of 5.038 mg, the following amounts of water were found:

5.196 mg, 5.196 mg, 4.969 mg, 5.082 mg, 5.037 mg; mean value: 5.096 mg.

EXAMPLE 4

50 ml of acetonitrile, which contain 0.05 mol/l of trimethylammonium iodide and 0.5 mol/l of the molar 1:1 trimethylamine-sulphur dioxide addition compound, are introduced into a divided cell for the coulometric Karl-Fischer titration. At the anode, iodine is generated, and at the cathode, hydrogen is generated.

After an iodine excess has been generated, a sample having a water content of between 2 and 5 mg is dosed. The indication takes place photometrically, as described in Example 2. The amount of electrical charge which has flowed in between the two equivalence-points is used to calculate the water content.

We claim:

1. A method for the quantitative determination of water in a water-containing sample, wherein the sample is mixed with about a molar 1:1 adduct of sulphur dioxide with an amine having a $pK_A$ of more than about 6, dissolved in an aprotic solvent excluding alcohols, is oxidized with iodine, the quantity of iodine consumed in said oxidation step is determined, and the quantity of water in said sample is calculated based upon said quantity of iodine consumed.

2. The method according to claim 1, wherein said amine is trimethylamine.

3. The method according to claim 1, wherein the quantitative determination of water is by a volumetric determination of water, the water-containing sample
   a) is mixed with the molar 1:1 adduct of sulphur dioxide to an amine, dissolved in the aprotic solvent, and is then titrated with an iodine solution, or
   b) is dissolved in an aprotic solvent and is titrated with a solution which, in an aprotic solvent, contains a molar 1:1 adduct of sulphur dioxide to an amine having a $pK_A$ or more than 6 and iodine.

4. The method according to claim 3, wherein said amine is trimethylamine.

5. The method according to claim 1, wherein the quantitative determination of water is by a coulometric determination of water, the water-containing sample is mixed with a solution in an aprotic solvent which, contains a molar 1:1 adduct of sulphur dioxide to an amine and a soluble iodide, and in that iodine is generated therefrom by anodic oxidation.

6. The method according to claim 5, wherein said amine is trimethylamine.

7. The reagent comprising a solvent component and an iodine solution as a titrant component for the quantitative determination of water in a water-containing sample, wherein said solvent component excludes alcohols and contains about a molar 1:1 adduct of sulphur dioxide to an amine having a $pK_A$ of more than about 6 in an aprotic solvent.

8. The reagent for the quantitative determination of water in a water-containing sample, comprising a molar 1:1 adduct of sulphur dioxide to an amine having a $pK_A$ of more than 6 in an aprotic solvent excluding alcohols and iodine or an iodide in an aprotic solvent excluding alcohols.

9. The reagent according to claim 8, wherein the amine is selected from the group consisting of trimethylamine, imidazole, N,N,N',N'-tetramethylethylenediamine and a mixture thereof.

10. The reagent according to claim 8, wherein the aprotic solvent is selected from the group consisting of an ether, ester, halogenated hydrocarbon, an acid amide, nitrile, ketone and a mixture thereof.

11. The reagent according to claim 9, wherein the aprotic solvent is selected from the group consisting of an ether, ester, halogenated hydrocarbon, an acid amide, nitrile, ketone and a mixture thereof.

12. The reagent according to claim 11, wherein the aprotic solvent is selected from the group consisting of acetonitrile, propylene carbonate, ethyl acetate, tetrahydrofuran, dioxane, dimethylformamide, methylene chloride and mixtures thereof.

13. The reagent according to claim 12, wherein a concentration of the molar 1:1 adduct in the solvent is from about 0.25 to about 1.5 mol/l.

14. The reagent according to claim 8, wherein a concentration of the molar 1:1 adduct in the solvent is from about 0.01 to about 5 mol/l.

15. The reagent according to claim 8, wherein said amine is trimethylamine.

* * * * *